United States Patent [19]

Goss

[11] Patent Number: 4,722,798

[45] Date of Patent: Feb. 2, 1988

[54] HEMODIALYSIS WITH DIALYSATE OSMOLARITY VARIED NON-LINEARLY WITH TIME

[75] Inventor: Jack Goss, Clearwater, Fla.

[73] Assignee: Baxter Travenol Laboratories, Inc., Deerfield, Ill.

[21] Appl. No.: 797,749

[22] Filed: Nov. 12, 1985

Related U.S. Application Data

[63] Continuation of Ser. No. 659,972, Oct. 12, 1984, abandoned, which is a continuation of Ser. No. 400,790, Jul. 22, 1982, abandoned, which is a continuation of Ser. No. 272,633, Jun. 11, 1981, abandoned.

[51] Int. Cl.$^4$ ............................................. B01D 13/00
[52] U.S. Cl. ..................................... 210/646; 210/647
[58] Field of Search ................ 210/637, 639, 644–648, 210/743, 746; 604/28, 29; 659/972

[56] References Cited

U.S. PATENT DOCUMENTS

| | | | |
|---|---|---|---|
| 3,418,209 | 12/1968 | Ushakoff | 422/41 X |
| 4,306,556 | 12/1981 | Zelman | 604/410 |
| 4,464,337 | 8/1984 | Zelman | 422/41 |
| 4,601,830 | 7/1986 | Chen | 210/647 |

FOREIGN PATENT DOCUMENTS 54-148181  11/1979  Japan ................................ 210/321.3

OTHER PUBLICATIONS

Holmes, J. H. et al, "Removal of Fluid from the Patient . . . " Trans. Am. Soc. Art. Int. Organs, vol. 5, 1959, pp. 58–68.

Maeda et al, "Hemodiafiltration with Sodium Concentration-Controlled Dialysate", Art. Organs, vol. 4, No. 2, May 1980, pp. 121–124.

Dumler, F. et al, "Sequential High/Low Sodium Hemodialysis, . . . " Trans. Am. Soc. Artif. Intern. Organs, vol. 25, 351-353; 1979.Inter Chen, W. et al, "Hydrostatic Ultrafiltration . . . ", Artificial Organs, vol. 4, No. 3, 8/1980, pp. 187–191.

Pasternack, A., "Engineering Aspects of Artificial Kidney . . . ", Int. Chem. Eng., vol. 16, No. 1, 1/1976, pp. 1–10.

Primary Examiner—David Sadowski
Attorney, Agent, or Firm—Paul C. Flattery; Daniel D. Ryan

[57] ABSTRACT

The invention is concerned with a hemodialysis technique employing a dialyzer having a blood flow compartment separated from a dialysate flow compartment by a semi-permeable membrane. According to the invention, this technique is improved by providing for the osmolarity of the dialysate to be increased as a function of time during at least a portion of the total treatment time, whereby dialysis disequilibrium syndrome problems can be alleviated.

2 Claims, 4 Drawing Figures

PRIOR ART—STANDARD DIALYSIS TREATMENT

PRIOR ART—"HIGH SODIUM" DIALYSIS

PRIOR ART-LINEAR DECREASE IN CONCENTRATION OF SODIUM ION IN DIALYSATE DURING FIRST HOUR OF TREATMENT

NON LINEAR VARIATION IN CONCENTRATION OF SODIUM ION IN DIALYSATE DURING FIRST STAGE OF TREATMENT CYCLE

HEMODIALYSIS WITH DIALYSATE OSMOLARITY VARIED NON-LINEARLY WITH TIME

CROSS REFERENCE TO RELATED APPLICATIONS

This application is a continuation of application Ser. No. 659,972 filed Oct. 12, 1984, now abandoned, which was a continuation of Ser. No. 400,790 filed July 22, 1982, now abandoned, which was a continuation of Ser. No. 272,633 filed June 11, 1981, now abandoned.

Field Of The Invention

This invention relates to a method and apparatus for performing hemodialysis. More particularly, the invention relates to method and apparatus for performing hemodialysis in which the osmolarity of the dialysis fluid varies, non-linearly as a function of time during at least a portion of the total time used for the treatment cycle.

BACKGROUND OF THE INVENTION

The use of dialysis to treat patients with kidney disease is well-known. The treatment involves the use of an artificial kidney dialyzer which is a device comprising a first compartment for the flow of blood to be dialyzed and a second compartment for the flow of an aqueous dialysis fluid (or "dialysate" as it is sometimes called). The two compartments are separated from one another in the device by a semipermeable membrane suitable for the dialysis procedure. Such semipermeable membranes are commercially available and are made from, for example, regenerated cuprammonium cellulose or cellulose acetate. The semipermeable membranes may be used in kidney dialyzers in the form of sheet, tubing or hollow fibers.

In its broadest aspect, hemodialysis involves withdrawing blood from a patient and passing that blood through the blood flow compartment of the artificial kidney while at the same time passing aqueous dialysis fluid through the dialysate compartment. As the blood flows through the dialyzer, impurities such as urea and creatinine are transported through the semipermeable membrane and are dissolved in the dialysate. Cleansed blood exiting the dialyzer is returned to the patient, while the dialysate containing the impurities removed from the blood is recirculated or discarded.

The dialysate comprises an aqueous solution of electrolytes which is prepared, either on a batch basis or continuously, by dissolving the electrolytes in water or by diluting a concentrated aqueous solution of the electrolytes (called a "dialysate concentrate") with water. In either case, the "standard" dialysate customarily used to carry out the dialysis treatment has a fixed composition which typically comprises about 136 milliequivalents per liter (meq./l.) of sodium ion, about 3.5 meq./l. of calcium ion, about 1.5 meq./l. of magnesium ion, about 2.6 meq./l. of potassium ion, about 106.6 meq./l. of chloride ion, and about 37 meq/l. of acetate ion. (In some instances, part or all of the acetate ion may be replaced by bicarbonate ion).

Since, as is well known, the conductivity of an aqueous solution of electrolytes is a function of the concentration of electrolytes dissolved therein, it is possible to ascertain whether the desired concentration of electrolytes is present in the dialysate being supplied to the dialysate compartment by measuring the conductivity of the dialysate. Thus a hemodialysis system typically comprises a conductivity cell which is placed in the dialysate line between the source of dialysate and the inlet to the dialysate compartment and which continuously monitors the conductivity of the entering dialysate. The conductivity cell has three electrodes uniformly spaced in an epoxy casing. Two of these electrodes are wired together internally and exit the cell body at a "common" terminal; the third of the electrodes exits the cell at a "signal" terminal. The conductivity cell is part of a conductivity monitor circuit which is designed to create a small voltage between the cell's "signal" and "common" terminal.

The amount of the flow of electrons which results from this voltage will depend upon the conductivity of the dialysate solution flowing through the conductivity cell. In the event the measured conductivity of the dialysate is more than a fixed amount, e.g. 5%, above or below the desired conductivity, the monitor circuit automatically sends a signal to its associated logic circuitry which, in turn, produces an alarm (either audible or visual or both) indicating that the dialysate conductivity limits have been exceeded. Since conductivity is also temperature dependent it is common practice to include a thermistor in the conductivity circuit. This thermistor, which is located on the inlet side of the conductivity cell, continuously feeds dialysate temperature information to the conductivity monitor circuit, thus allowing that circuit to compensate for any changes in dialysate temperature. Thus it will be seen that the conductivity cell measures the dialysate conductivity on a continuous basis and sounds an alarm if that conductivity deviates more or less than a fixed amount from a constant conductivity value.

Figure 1:
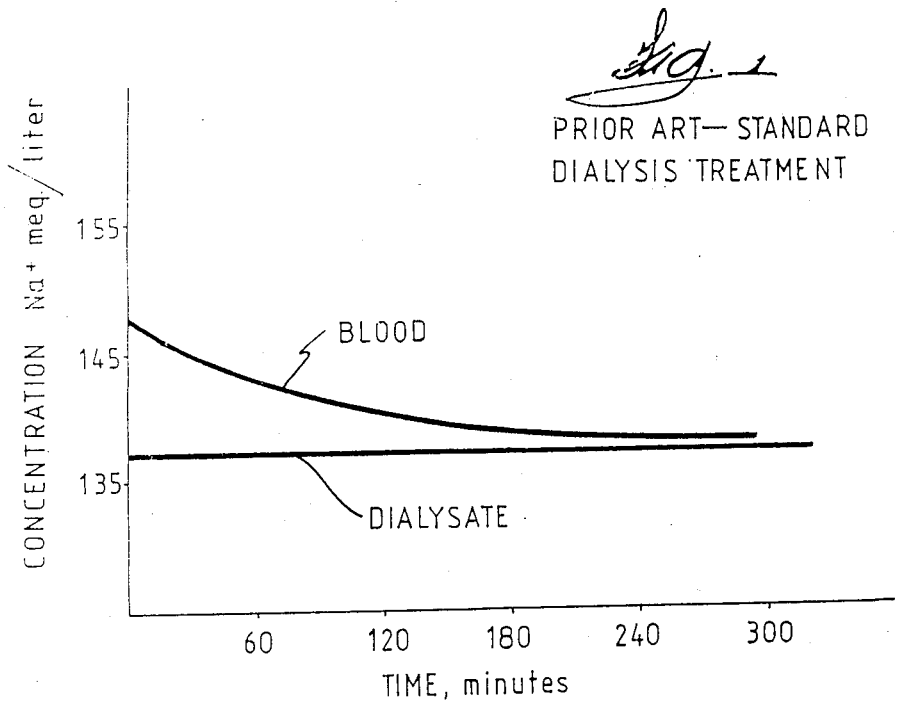
FIG. 1 is a graph showing the sodium ion concentration in the blood during a prior art, "standard" method of hemodialysis in which the sodium ion concentration in the dialysate during the treatment cycle is lower than the sodium ion concentration in the blood and the composition of the dialysate is kept constant for the duration of the treatment cycle.

A patient with kidney disease is typically on a treatment schedule in which his blood is dialyzed every third day, the duration of the treatment varying on the order of from about three to about five hours. At the beginning of a treatment, the sodium ion level in the patient's blood is elevated and is in the range of 145-146 meq./liter. In what is regarded as a standard dialysis treatment, the patient's blood is dialyzed against the aforementioned, fixed composition standard dialysate, which has a sodium ion concentration of 136 meq./liter. The composition of the dialysate solution, and hence the osmolarity, is kept constant for the duration of the treatment cycle. Thus, as illustrated in FIG. 1, the sodium ion concentration in the patient's blood is gradually reduced so that at the end of the treatment, the blood sodium concentration has been reduced to a level which is approximately equal to the dialysate sodium concentration. The osmolarity of the patient's blood has also been reduced as a result of the removal therefrom of both ionized and non-ionized waste products during the dialysis treatment. In the time prior to his next scheduled treatment, the sodium ion level in the patient's blood gradually increases so that just prior to the start of the next treatment, it has reached the elevated level of 145-146 meq./liter. The increase in sodium ion, along with increases in the concentration of non-ionizable waste products, results in a corresponding increase in the patient's blood osmolarity.

It has been observed that patients who are dialyzed after a lay-off of several days exhibit what is known as "dialysis disequilibrium syndrome", that is, the patient suffers from such symptoms as nausea, headache, and vomiting. Dialysis disequilibrium syndrome is thought to be related to the large difference between the total blood osmolarity of the patient at the outset of the dialysis treatment compared to the total osmolarity of the dialysate being used.

Figure 2:
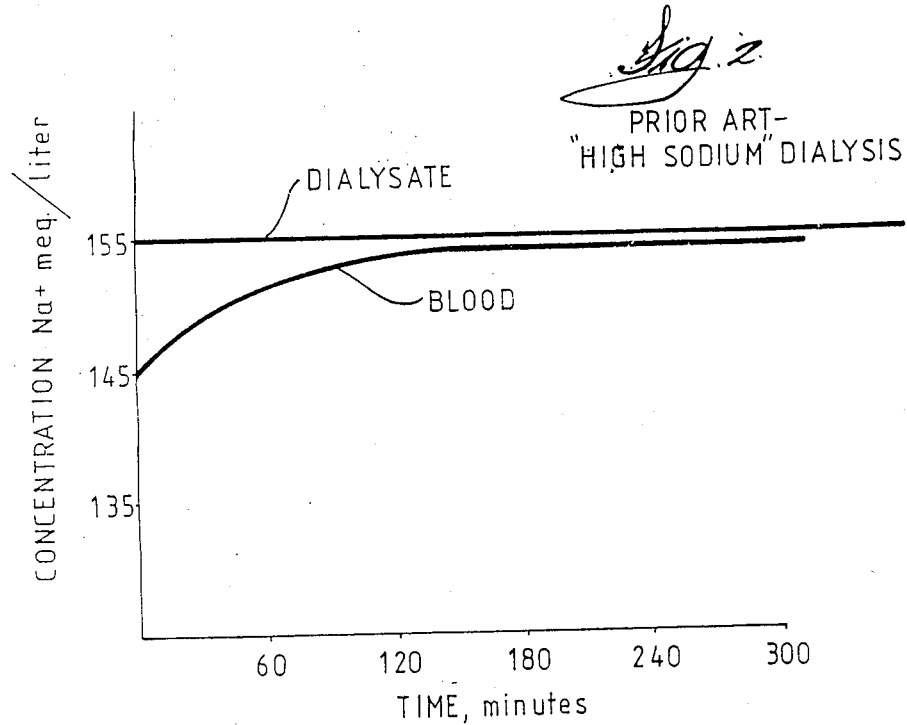
FIG. 2 is a graph showing the sodium ion concentration in the blood during a prior art, so-called "high sodium" method of hemdialysis in which the sodium ion concentration in the dialysate during the treatment cycle is higher than the sodium ion concentration in the blood and the composition of the dialysate is kept constant for the duration of the treatment cycle.

It has been proposed in order to alleviate dialysis disequilibrium syndrome that the sodium ion concentration in the dialysate be increased which in turn increases the total dialysate osmolarity. In one approach, illustrated in FIG. 2, "high sodium dialysate" is used for the duration of the treatment. The dialysate solution used in this "high sodium dialysate" approach has a sodium ion concentration of about 155 meq./liter as a result of which its osmolarity is significantly higher than the total blood osmolarity of the patient at the start of the treatment. It will be understood that this approach does not involve any change in the osmolarity of the dialysate during the treatment; the osmolarity of the dialysate is maintained constant throughout the treatment cycle although at a level which is higher than the osmolarity of the aforementioned standard dialysate. While this approach appears to have enjoyed some success in relieving dialysis disequilibrium syndrome and does not interfere with the removal from the blood of such impurities as urea and creatinine, it suffers from the serious disadvantage that during the dialysis treatment cycle, the sodium ion level in the patient's blood increases, whereas one of the purposes of dialysis is to reduce such sodium levels. In addition, such elevation in blood sodium level tends to make the patient thirsty, and he desires to drink water to alleviate that thirst at precisely the time when it is desired to reduce the patient's body water content via ultrafiltration during the dialysis procedure.

Figure 3:
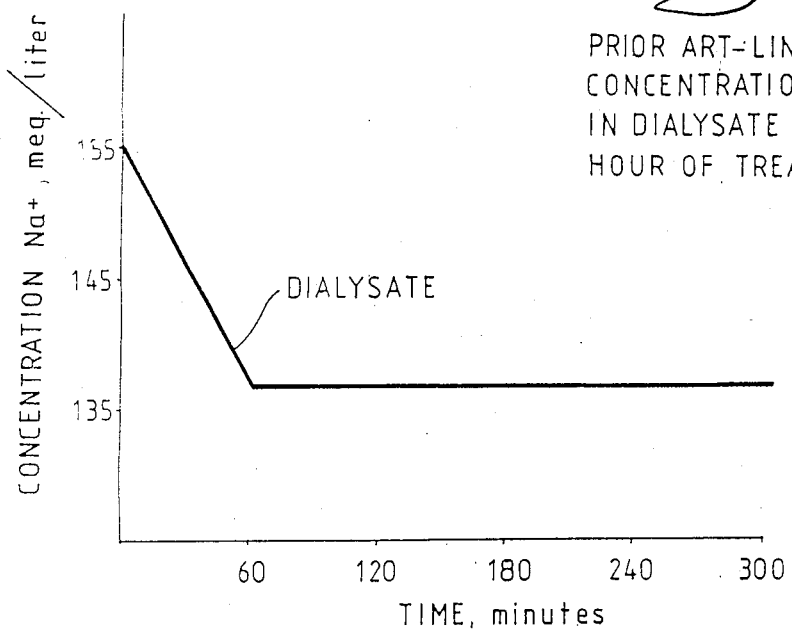
FIG. 3 is a graph showing the sodium ion concentration of the dialysate as a function of time in a prior art method of hemodialysis in which the sodium ion concentration in the dialysate is decreased linearly during, for example, the first hour of treatment and is held constant during the remainder of the treatment.

In a second approach to alleviating the dialysis disequilibrium syndrome problem, a supplementary aqueous sodium ion solution (e.g., a solution of sodium chloride in water) is used in conjunction with the aforementioned "standard" dialysate solution having a fixed composition. In this approach, standard dialysate is continuously fed to the dialysate compartment in the usual way, and the supplementary aqueous sodium ion solution is added at a linearly decreasing rate for an initial portion of the treatment time and at a constant rate for the remainder of the treatment time. Thus, the osmolarity of the dialysate flowing through the dialysate compartment of the dialyzer is linearly reduced during the initial stages of the dialysis treatment cycle. As an example of the second approach, and assuming the patient's total blood sodium level at the outset of the treatment to be 145 meq./l., the supplementary aqueous sodium ion solution is added to the dialysate (136 meq./l. Na+) at an initial rate such that the dialysate which initially flows through the dialyzer has a sodium ion concentration of about 155 meq./l. The rate of addition of the supplementary sodium ion solution to the standard dialysate solution is then continuously reduced on a linear basis so that, by the end of an initial portion (e.g., one hour) of the total dialysis treatment cycle time, the overall concentration of sodium ion in the dialysate has approached the customarily used level of about 136 meq./l. At that point, the addition of the supplementary sodium ion is discontinued (or, if it is desired to keep the feed line flushed, kept at a constant, extremely low rate) so that the sodium ion level in the dialysate for the remainder of the treatment time is held substantially constant at the customary level of about 136 meq./l. See FIG. 3. The disadvantages of this second approach are similar, though perhaps not so severe, to those encountered with the first described approach. During the initial stages of the dialysis treatent the total dialysate osmolarity is undesirably and disadvantageously higher than the patient's total blood osmolarity. The patient's blood sodium level rises sharply during the first thirty minutes of the treatment instead of falling as is desirable. The patient still experiences thirst and desires to take in water at exactly the time when his water content is supposed to be reduced or at least held constant.

In accordance with the present invention there is provided an improved method for dialyzing blood. The improved method helps to alleviate the symptoms of, and the problems associated with, dialysis disequilibrium syndrome and is characterized by the fact that the osmolarity of the dialysate supplied to the dialysate chamber of an artificial kidney is varied non-linearly as a function of time during at least a portion of the total time used for the dialysis treatment cycle. In a specific embodiment of the improved method, the osmolarity of a standard dialysate solution is varied by varying the concentration of sodium ion in the dialysate solution in accordance with the equation:

$$y = [Ut - U(t-8)] \, 100 \sin \frac{\pi t}{10} + [U(t-8) - U(t-17)]$$

$$\left( -\frac{t^3}{3} + 12.5t^2 - 150t + 628.33 \right) +$$

$$[U(t-17) - U(t-60)](-t+70) + [U(t-60)]10$$

where y = the concentration of sodium ion in the dialysate, t is the time in minutes and U is a Unit Step Function.

A preferred method according to the present invention employs the standard fixed composition dialysate solution described earlier herein, and a supplementary aqueous solution of sodium ion. The supplementary solution preferably consists of sodium chloride dissolved in water. A 10% by weight solution of sodium chloride in water has been found suitable, although other concentrations of sodium chloride may be used. Similarly, other ionizable sodium salts may be used in place of sodium chloride. The osmolarity of the dialysate flowing through the dialysate compartment of the dialyzer is varied on a non-linear basis during the first part of the treatment cycle. The length of this first part of time during which the dialysate osmolarity is varied on a non-linear basis may be, for example, one, two, or three hours. After the first part of the total treatment time has been completed, the osmolarity of the dialysate is preferably decreased linearly until it approaches the osmolarity of standard dialysate. From that point in time until the treatment is completed, the osmolarity of the dialysate is maintained substantially constant at its standard level.

EXAMPLE I

Following is an example of a dialysis treatment in which the osmolarity of the dialysate is varied non-linearly during the first hour of a five-hour treatment and is maintained substantially constant for the last four hours. During the first hour of the treatment, the dialysate supplied to the dialysate chamber of the dialyzer consists of a mixture of the earlier-described standard dialysate solution having a fixed composition and a supplementary aqueous solution of 10% by weight sodium chloride. The osmolarity of the supplied dialysate is varied by varying the sodium ion concentration therein. The sodium ion concentration in the supplied dialysate is varied by changing the amount of the supplementary solution which is mixed with the standard dialysate.

A patient having kidney disease is set up in the usual fashion for a dialysis treatment. Blood to be dialyzed is taken from the patient, pumped through a blood dialyzer, and returned to the patient as usual. An aqueous solution consisting of 136 meq./l. $Na^+$, 106.6 meq./l. $Cl^-$, 3.5 meq./l. $Ca^{+2}$, 1.5 meq./l. $Mg^{+2}$, 2.6 meq./l. $K^+$, and 37 meq./l. of acetate ion is used as the standard dialysate of fixed composition. A solution of 10% by weight of sodium chloride in water is used as the supplementary aqueous sodium ion solution, this solution containing 380 meq./l. sodium ion. The standard dialysate solution and the supplementary solution are kept in separate reservoirs and are pumped to a mixing point on the inlet side of the dialysate chamber using any suitable pumping means. The standard dialysate is pumped at a rate of 0.5 liters/minute. The patient to be treated has a total blood sodium level at the start of the treatment of about 145–146 meq./l. At the outset of the treatment and for approximately three minutes thereafter, the supplementary solution is added to the standard dialysate at such a rate that the sodium ion concentration in the mixed dialysate entering the dialyzer rises to a value of about 155 meq./l. It will be observed that the sodium ion concentration in the mixed dialysate (and, correspondingly, the osmolarity) at this point in the treatment cycle is considerably in excess of the initial sodium ion concentration of the patient's blood. Subsequently, the rate of addition of the supplementary solution is reduced so that after about 10 minutes from the start of the treatment, the sodium ion concentration in the mixed dialysate is about 145 meq./l. At the end of the same ten minute period, the sodium ion level in the patient's blood has increased to a level of approximately 150 meq./l. It will be observed that, at this point in the treatment cycle, the sodium ion level in (and, correspondingly, the osmolarity of) the mixed dialysate is decreasing, while the sodium ion concentration of the patient's blood is increasing. It should further be noted that at this point in time the sodium level in the mixed dialysate is less than the sodium ion level in the patient's blood. The rate of addition of the supplementary solution is then increased and during the next 6 minutes of the treatment cycle, the sodium ion concentration in the mixed dialysate reaches 148 meq./l. while the sodium ion concentration in the blood reaches a level of 152 meq./l.

As a result of the foregoing procedure, the peak value of the sodium ion in the blood is minimized during the first thirty minutes of the treatment. The time lag between the increase in sodium ion level in the dialysate and the subsequent increase in the sodium ion level in the blood is significant in holding the peak levels of sodium ion in the blood to a minimum. Subsequently, the rate of addition of the supplementary solution is reduced gradually and on a linear basis until the sodium ion concentration in the dialysate supplied to the dialyzer approaches 136 meq./liter which is the sodium ion concentration in the standard, fixed composition dialysate. At that time, the addition of the supplementary solution is substantially discontinued (if desired, the addition of the supplementary solution may be continued at a negligible rate in order to keep the feed lines flushed) and the sodium ion concentration in the dialysate (and hence the osmolarity of the dialysate) is held substantially constant for the remainder of the treatment cycle.

Figure 4:
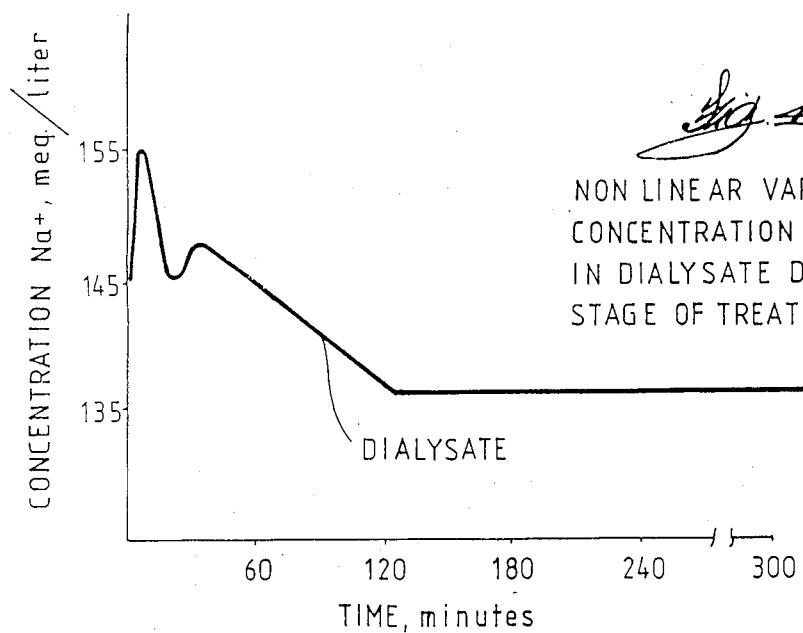
FIG. 4 is a graph showing the sodium ion concentration of the dialysate as a function of time during practice of one embodiment of the inventive method in which the concentration of the sodium ion in the dialysate is both increased and decreased during an early stage of the treatment cycle.

It will be understood that a variation in the sodium ion level in the dialysate effects a corresponding variation in the dialysate osmolarity, that is, a higher sodium ion level produces a higher osmolarity and a lower sodium ion level produces lower osmolarity. FIG. 4 shows the nonlinear variation of the sodium ion level in the dialysate during the initial stages of the treatment, the subsequent linear decrease in concentration of the sodium ion in the dialysate in the intermediate stages of the treatment, and the constant level of sodium ion in the dialysate during the final stages of the treatment. Since the osmolarity is a direct function of the sodium ion level, the osmolarity of the dialysate likewise varies non-linearly, then decreases linearly, and thereafter holds constant for the remainder of the treatment.

I claim:
1. A method of treating a patient with kidney disease with hemdialysis which method includes the steps of:
   (a) providing a dialyzer having a blood flow compartment separated from a dialysate flow compartment by a semi-permeable membrane,
   (b) conducting blood from said patient to be dialyzed through said blood flow compartment,
   (c) conducting a dialysate solution through said dialysate flow compartment, and
   (d) immediately returning blood from said blood flow compartment back to said patient, wherein the improvement comprises both increasing and decreasing the osmolarity of said dialysate solution as a function of time during at least a portion of the total time used for said treatment by changing the concentration of sodium ions in said dialysate solution to alleviate dialysis disequilibrium syndrome in the patient by the steps comprising:

(1) during an initial portion of the treatment, increasing the osmolarity of the dialysate solution from an initial value to a higher first maximum value,
(2) thereafter, reducing the osmolarity of the dialysate solution from the first maximum value to a first minimum value which is higher than the initial value,
(3) thereafter increasing the osmolarity of the dialysate solution from the first minimum value to a second maximum value which is less than the first maximum value,
(4) thereafter decreasing the osmolarity of the dialysate solution from the second maximum value to the initial value, and
(5) thereafter maintaining the osmolarity of the dialysate solution substantially at the initial value for the remaining portion of the treatment.

2. A method according to claim 1 wherein said dialysate solution is formed by mixing a dialysate solution of fixed composition with a supplementary solution comprising an ionizable substance.

* * * * *